(12) United States Patent
Beaurain et al.

(10) Patent No.: US 8,267,999 B2
(45) Date of Patent: *Sep. 18, 2012

(54) INTERVERTEBRAL DISC PROSTHESIS

(75) Inventors: Jacques Beaurain, Sauton la Chapelle (FR); Jean-Marc Fuentes, Grebels (FR); Jean-Marc Vital, Bordeaux (FR); Thierry Dufout, Oliver (FR); Jean Huppert, L'Etral (FR)

(73) Assignee: LDR Medical, Rosières Près Troyes (FR)

( * ) Notice: Subject to any disclaimer, the term of this patent is extended or adjusted under 35 U.S.C. 154(b) by 251 days.

This patent is subject to a terminal disclaimer.

(21) Appl. No.: 12/424,364

(22) Filed: Apr. 15, 2009

(65) Prior Publication Data
US 2009/0204219 A1 Aug. 13, 2009

Related U.S. Application Data

(63) Continuation of application No. 10/533,846, filed as application No. PCT/IB03/04872 on Oct. 31, 2003, now Pat. No. 7,682,396.

(30) Foreign Application Priority Data

Nov. 5, 2002 (FR) ...................................... 02 13833

(51) Int. Cl.
*A61F 2/44* (2006.01)
(52) U.S. Cl. ................. 623/17.14; 623/17.11; 623/17.15
(58) Field of Classification Search ..... 623/17.11–17.16
See application file for complete search history.

(56) References Cited

U.S. PATENT DOCUMENTS
566,360 A 8/1896 White
(Continued)

FOREIGN PATENT DOCUMENTS
CA 2472708 2/2005
(Continued)

OTHER PUBLICATIONS

A biological basis for instantaneous centres of rotation of the vertebral column, N. Bonduk, B. Amevo, J. Pearcy, Proc Institution Mechanical Engineers, Jun. 16, 1995, pp. 177-183.

(Continued)

*Primary Examiner* — Andrew Yang
(74) *Attorney, Agent, or Firm* — Denko Coburn & Lauff LLP

(57) ABSTRACT

The present invention relates to an intervertebral disk prosthesis comprising at least three parts including a first plate, referred to as the upper plate (1), a second plate, referred to as the lower plate (2), and a core (3), the upper surface of the core (3) being in contact with at least part (10) of the lower surface of the upper plate (1) and the lower surface of the core (3) being in contact with at least part of the upper surface of the lower plate (2), and the lower plate (1) being movable at least with respect to the core (3), characterized in that there are cooperation means between the lower to plate (2) and the core (3), so as to limit or eliminate translation movements of the core (3) with respect to the lower plate (2) along an axis substantially parallel to the lower plate (2), and to limit or eliminate rotation movements of the core (3) with respect to the lower plate (2), around an axis substantially perpendicular to the lower plate (2), the planes passing through the upper (1) is and lower (2) plates forming a substantially constant angle.

22 Claims, 4 Drawing Sheets

U.S. PATENT DOCUMENTS

| | | |
|---|---|---|
| 1,436,573 A | 11/1922 | Choppinet et al. |
| 2,836,442 A | 5/1958 | Moskovitz |
| 3,325,197 A | 6/1967 | Wehner |
| 3,374,786 A | 3/1968 | Callender et al. |
| 3,486,505 A | 12/1969 | Morrison |
| 3,791,380 A | 2/1974 | Dawidowski |
| 3,857,642 A | 12/1974 | Miller |
| 3,892,232 A | 7/1975 | Neufeld |
| 3,958,278 A | 5/1976 | Lee et al. |
| 4,009,712 A | 3/1977 | Burstein et al. |
| 4,074,542 A | 2/1978 | Hankosky et al. |
| 4,085,466 A | 4/1978 | Goodfellow et al. |
| 4,135,506 A | 1/1979 | Ulrich |
| 4,175,555 A | 11/1979 | Herbert |
| 4,185,762 A | 1/1980 | Froehlich |
| 4,237,875 A | 12/1980 | Termanini |
| 4,309,777 A | 1/1982 | Patil |
| 4,349,921 A | 9/1982 | Kuntz |
| 4,379,451 A | 4/1983 | Getscher |
| 4,409,974 A | 10/1983 | Freedland |
| 4,432,358 A | 2/1984 | Fixel |
| 4,488,543 A | 12/1984 | Tornier |
| 4,494,535 A | 1/1985 | Haig |
| 4,519,100 A | 5/1985 | Wills et al. |
| 4,561,432 A | 12/1985 | Mazor |
| 4,612,920 A | 9/1986 | Lower |
| 4,621,629 A | 11/1986 | Koeneman |
| 4,632,101 A | 12/1986 | Freedland |
| 4,653,489 A | 3/1987 | Tronzo |
| 4,655,778 A | 4/1987 | Koeneman |
| 4,657,001 A | 4/1987 | Fixel |
| 4,664,305 A | 5/1987 | Blake, III et al. |
| 4,714,469 A | 12/1987 | Kenna |
| 4,721,103 A | 1/1988 | Freedland |
| 4,756,711 A | 7/1988 | Mai et al. |
| 4,759,352 A | 7/1988 | Lozier |
| 4,759,766 A | 7/1988 | Buettner-Janz et al. |
| 4,759,769 A | 7/1988 | Hedman et al. |
| 4,787,378 A | 11/1988 | Sodhi |
| 4,787,908 A | 11/1988 | Wyss et al. |
| 4,790,303 A | 12/1988 | Steffee |
| 4,791,918 A | 12/1988 | Von Hasselbach |
| 4,863,476 A | 9/1989 | Sheppard |
| 4,874,389 A | 10/1989 | Downey |
| 4,892,545 A | 1/1990 | Day et al. |
| 4,898,156 A | 2/1990 | Gatturna et al. |
| 4,911,718 A | 3/1990 | Lee et al. |
| 4,932,975 A | 6/1990 | Main et al. |
| 4,946,378 A | 8/1990 | Hirayama et al. |
| 4,946,468 A | 8/1990 | Li |
| 4,955,908 A | 9/1990 | Frey et al. |
| 4,955,916 A | 9/1990 | Carignan et al. |
| 4,964,403 A | 10/1990 | Karas et al. |
| 4,968,315 A | 11/1990 | Gatturna |
| 4,969,887 A | 11/1990 | Sodhi |
| 4,973,332 A | 11/1990 | Kummer |
| 4,973,333 A | 11/1990 | Treharne |
| 4,997,432 A | 3/1991 | Keller |
| 5,002,550 A | 3/1991 | Li |
| 5,002,576 A | 3/1991 | Fuhrmann et al. |
| 5,007,910 A | 4/1991 | Anapliotis et al. |
| 5,032,125 A | 7/1991 | Durham et al. |
| 5,041,114 A | 8/1991 | Chapman et al. |
| 5,041,116 A | 8/1991 | Wilson |
| 5,041,139 A | 8/1991 | Branemark |
| 5,046,513 A | 9/1991 | Gatturna et al. |
| 5,057,103 A | 10/1991 | Davis |
| 5,062,851 A | 11/1991 | Branemark |
| 5,071,437 A | 12/1991 | Steffee |
| 5,087,266 A | 2/1992 | Connell et al. |
| 5,098,433 A | 3/1992 | Freedland |
| 5,116,336 A | 5/1992 | Frigg |
| 5,122,130 A | 6/1992 | Keller |
| 5,123,926 A | 6/1992 | Pisharodi |
| 5,129,901 A | 7/1992 | Decoste |
| 5,171,281 A | 12/1992 | Parsons et al. |
| 5,176,681 A | 1/1993 | Lawes et al. |
| 5,192,303 A | 3/1993 | Gatturna et al. |
| 5,192,327 A | 3/1993 | Brantigan |
| 5,197,986 A | 3/1993 | Mikhail |
| 5,207,679 A | 5/1993 | Li |
| 5,217,486 A | 6/1993 | Rice et al. |
| 5,234,447 A | 8/1993 | Kaster et al. |
| 5,242,448 A | 9/1993 | Pettine et al. |
| 5,246,458 A | 9/1993 | Graham |
| 5,258,009 A | 11/1993 | Conners |
| 5,258,031 A | 11/1993 | Salib et al. |
| 5,290,312 A | 3/1994 | Kojimoto et al. |
| 5,300,074 A | 4/1994 | Frigg |
| 5,306,309 A | 4/1994 | Wagner et al. |
| 5,314,477 A | 5/1994 | Marnay |
| 5,324,292 A | 6/1994 | Meyers |
| 5,342,394 A | 8/1994 | Matsuno et al. |
| 5,356,410 A | 10/1994 | Pennig |
| 5,356,413 A | 10/1994 | Martins et al. |
| 5,358,526 A | 10/1994 | Tornier |
| 5,370,697 A | 12/1994 | Baumgartner |
| 5,372,599 A | 12/1994 | Martins |
| 5,397,364 A | 3/1995 | Kozak et al. |
| 5,401,269 A | 3/1995 | Buttner-Janz et al. |
| 5,417,692 A | 5/1995 | Goble et al. |
| 5,417,712 A | 5/1995 | Whittaker et al. |
| 5,425,773 A | 6/1995 | Boyd et al. |
| 5,429,641 A | 7/1995 | Gotfried |
| 5,437,674 A | 8/1995 | Worcel et al. |
| 5,456,721 A | 10/1995 | Legrand |
| 5,458,601 A | 10/1995 | Young, Jr. et al. |
| 5,472,452 A | 12/1995 | Trott |
| 5,478,342 A | 12/1995 | Kohrs |
| 5,489,210 A | 2/1996 | Hanosh |
| 5,507,754 A | 4/1996 | Green et al. |
| 5,507,816 A | 4/1996 | Bullivant |
| 5,522,845 A | 6/1996 | Wenstrom, Jr. |
| 5,522,899 A | 6/1996 | Michelson |
| 5,531,792 A | 7/1996 | Huene |
| 5,534,004 A | 7/1996 | Santangelo |
| 5,534,029 A | 7/1996 | Shima |
| 5,534,030 A | 7/1996 | Navarro et al. |
| 5,545,229 A | 8/1996 | Parsons et al. |
| 5,549,617 A | 8/1996 | Green et al. |
| 5,554,191 A | 9/1996 | Lahille et al. |
| 5,556,431 A | 9/1996 | Buttner-Janz et al. |
| 5,562,689 A | 10/1996 | Green et al. |
| 5,562,738 A | 10/1996 | Boyd et al. |
| 5,571,104 A | 11/1996 | Li |
| 5,571,109 A | 11/1996 | Bertagnoli |
| 5,571,189 A | 11/1996 | Kuslich |
| 5,578,035 A | 11/1996 | Lin |
| 5,591,168 A | 1/1997 | Judet et al. |
| 5,593,409 A | 1/1997 | Michelson |
| 5,609,635 A | 3/1997 | Michelson |
| 5,609,636 A | 3/1997 | Kohrs et al. |
| 5,613,974 A | 3/1997 | Andreas et al. |
| 5,620,012 A | 4/1997 | Benderev et al. |
| 5,643,321 A | 7/1997 | McDevitt |
| 5,645,596 A | 7/1997 | Kim |
| 5,655,698 A | 8/1997 | Yoon et al. |
| 5,674,294 A | 10/1997 | Bainville et al. |
| 5,676,701 A | 10/1997 | Yuan et al. |
| 5,676,702 A | 10/1997 | Ratron |
| 5,683,465 A | 11/1997 | Shinn et al. |
| 5,702,449 A | 12/1997 | McKay |
| 5,702,450 A | 12/1997 | Bisserie |
| 5,702,472 A | 12/1997 | Huebner |
| 5,722,977 A | 3/1998 | Wilhelmy |
| 5,741,253 A | 4/1998 | Michelson |
| 5,766,252 A | 6/1998 | Henry et al. |
| 5,766,253 A | 6/1998 | Brosnahan, III |
| 5,772,661 A | 6/1998 | Michelson |
| 5,776,199 A | 7/1998 | Michelson |
| 5,782,832 A | 7/1998 | Larsen et al. |
| 5,782,919 A | 7/1998 | Zdeblick et al. |
| 5,797,909 A | 8/1998 | Michelson |
| 5,800,547 A | 9/1998 | Schafer et al. |
| 5,800,550 A | 9/1998 | Sertich |
| 5,807,403 A | 9/1998 | Beyar et al. |
| 5,824,094 A | 10/1998 | Serhan et al. |

| | | |
|---|---|---|
| 5,827,328 A | 10/1998 | Buttermann |
| 5,865,848 A | 2/1999 | Baker |
| 5,888,224 A | 3/1999 | Beckers et al. |
| 5,888,226 A | 3/1999 | Rogozinski |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima et al. |
| 5,968,098 A | 10/1999 | Winslow |
| 5,980,522 A | 11/1999 | Koros et al. |
| 5,984,967 A | 11/1999 | Zdeblick et al. |
| 6,001,130 A | 12/1999 | Bryan et al. |
| 6,010,502 A | 1/2000 | Bagby |
| 6,033,438 A | 3/2000 | Bianchi et al. |
| 6,039,763 A | 3/2000 | Shelokov |
| 6,045,552 A | 4/2000 | Zucherman et al. |
| 6,063,088 A | 5/2000 | Winslow |
| 6,063,121 A | 5/2000 | Xavier et al. |
| 6,066,175 A | 5/2000 | Henderson et al. |
| 6,080,158 A | 6/2000 | Lin |
| 6,093,205 A | 7/2000 | McLeod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,113,637 A | 9/2000 | Gill et al. |
| 6,113,638 A | 9/2000 | Williams et al. |
| 6,129,763 A | 10/2000 | Chauvin et al. |
| 6,136,031 A | 10/2000 | Middleton |
| 6,146,421 A | 11/2000 | Gordon et al. |
| 6,146,422 A | 11/2000 | Lawson |
| 6,149,650 A | 11/2000 | Michelson |
| 6,156,067 A | 12/2000 | Bryan et al. |
| 6,179,873 B1 | 1/2001 | Zientek |
| 6,179,874 B1 | 1/2001 | Cauthen |
| 6,193,757 B1 | 2/2001 | Foley et al. |
| 6,206,922 B1 | 3/2001 | Zdeblick et al. |
| 6,210,412 B1 | 4/2001 | Michelson |
| 6,214,050 B1 | 4/2001 | Huene |
| 6,221,077 B1 | 4/2001 | Rinner et al. |
| 6,224,595 B1 | 5/2001 | Michelson |
| 6,224,607 B1 | 5/2001 | Michelson |
| 6,228,118 B1 | 5/2001 | Gordon |
| 6,231,609 B1 | 5/2001 | Mehdizadeh |
| 6,241,769 B1 | 6/2001 | Nicholson et al. |
| 6,245,072 B1 | 6/2001 | Zdeblick et al. |
| 6,258,094 B1 | 7/2001 | Nicholson et al. |
| 6,261,293 B1 | 7/2001 | Nicholson et al. |
| 6,264,656 B1 | 7/2001 | Michelson |
| 6,267,763 B1 | 7/2001 | Castro |
| 6,270,498 B1 | 8/2001 | Michelson |
| 6,277,149 B1 | 8/2001 | Boyle et al. |
| 6,283,998 B1 | 9/2001 | Eaton |
| 6,287,308 B1 | 9/2001 | Betz et al. |
| 6,296,664 B1 | 10/2001 | Middleton |
| 6,302,914 B1 | 10/2001 | Michelson |
| 6,306,170 B2 | 10/2001 | Ray |
| 6,315,797 B1 | 11/2001 | Middleton |
| 6,319,257 B1 | 11/2001 | Carignan et al. |
| 6,342,074 B1 | 1/2002 | Simpson |
| 6,344,057 B1 | 2/2002 | Rabbe et al. |
| 6,364,880 B1 | 4/2002 | Michelson |
| 6,368,350 B1 | 4/2002 | Erickson et al. |
| 6,371,987 B1 | 4/2002 | Weiland et al. |
| 6,371,988 B1 | 4/2002 | Pafford et al. |
| 6,375,655 B1 | 4/2002 | Zdeblick et al. |
| 6,387,130 B1 | 5/2002 | Stone et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,413,278 B1 | 7/2002 | Marchosky |
| 6,416,551 B1 | 7/2002 | Keller |
| 6,419,703 B1 | 7/2002 | Fallin et al. |
| 6,419,704 B1 | 7/2002 | Ferree |
| 6,419,706 B1 * | 7/2002 | Graf .................. 623/17.16 |
| 6,423,063 B1 | 7/2002 | Bonutti |
| 6,423,095 B1 | 7/2002 | Van Hoeck et al. |
| 6,440,168 B1 | 8/2002 | Cauthen |
| 6,447,512 B1 | 9/2002 | Landry et al. |
| 6,447,544 B1 | 9/2002 | Michelson |
| 6,447,546 B1 | 9/2002 | Bramlet et al. |
| 6,447,547 B1 | 9/2002 | Michelson |
| 6,468,310 B1 | 10/2002 | Ralph et al. |
| 6,471,724 B2 | 10/2002 | Zdeblick et al. |
| 6,478,800 B1 | 11/2002 | Fraser et al. |
| 6,478,823 B1 | 11/2002 | Michelson |
| 6,482,234 B1 | 11/2002 | Weber et al. |
| 6,485,517 B1 | 11/2002 | Michelson |
| 6,500,205 B1 | 12/2002 | Michelson |
| 6,506,216 B1 | 1/2003 | McCue et al. |
| 6,514,260 B1 | 2/2003 | Zdeblick et al. |
| 6,517,580 B1 | 2/2003 | Ramadan et al. |
| 6,520,967 B1 | 2/2003 | Cauthen |
| 6,520,996 B1 | 2/2003 | Manasas et al. |
| 6,524,312 B2 | 2/2003 | Landry et al. |
| 6,527,804 B1 | 3/2003 | Gauchet et al. |
| 6,527,806 B2 | 3/2003 | Ralph et al. |
| 6,540,785 B1 | 4/2003 | Gill et al. |
| 6,558,423 B1 | 5/2003 | Michelson |
| 6,558,424 B2 | 5/2003 | Thalgott |
| 6,565,605 B2 | 5/2003 | Goble et al. |
| 6,572,653 B1 | 6/2003 | Simonson |
| 6,579,291 A | 6/2003 | Keith et al. |
| 6,579,320 B1 | 6/2003 | Gauchet et al. |
| 6,582,468 B1 | 6/2003 | Gauchet et al. |
| 6,592,624 B1 | 7/2003 | Fraser et al. |
| 6,599,320 B1 | 7/2003 | Kuslich et al. |
| 6,607,530 B1 | 8/2003 | Carl et al. |
| 6,607,558 B2 | 8/2003 | Kuras |
| 6,610,089 B1 | 8/2003 | Liu et al. |
| 6,610,092 B2 | 8/2003 | Ralph et al. |
| 6,610,093 B1 * | 8/2003 | Pisharodi .................. 623/17.15 |
| 6,613,091 B1 | 9/2003 | Zdeblick et al. |
| 6,616,671 B2 | 9/2003 | Landry et al. |
| 6,641,614 B1 | 11/2003 | Wagner et al. |
| 6,645,206 B1 | 11/2003 | Zdeblick et al. |
| 6,645,249 B2 | 11/2003 | Ralph et al. |
| 6,648,893 B2 | 11/2003 | Dudasik |
| 6,652,533 B2 | 11/2003 | O'Neil |
| 6,652,586 B2 | 11/2003 | Hunter et al. |
| 6,656,224 B2 | 12/2003 | Middleton |
| 6,669,730 B2 | 12/2003 | Ralph et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,679,887 B2 | 1/2004 | Nicholson et al. |
| 6,679,915 B1 | 1/2004 | Cauthen |
| 6,682,562 B2 | 1/2004 | Viart et al. |
| 6,695,851 B2 | 2/2004 | Zdeblick et al. |
| 6,695,882 B2 | 2/2004 | Bianchi et al. |
| 6,706,068 B2 | 3/2004 | Ferree |
| 6,709,439 B2 | 3/2004 | Rogers et al. |
| 6,709,458 B2 | 3/2004 | Michelson |
| 6,716,247 B2 | 4/2004 | Michelson |
| 6,719,794 B2 | 4/2004 | Gerber et al. |
| 6,723,127 B2 | 4/2004 | Ralph et al. |
| 6,723,128 B2 | 4/2004 | Uk |
| 6,726,720 B2 | 4/2004 | Ross et al. |
| 6,730,088 B2 | 5/2004 | Yeh |
| 6,733,504 B2 | 5/2004 | Lin et al. |
| 6,733,532 B1 | 5/2004 | Gauchet et al. |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,749,635 B1 | 6/2004 | Bryan |
| 6,749,636 B2 | 6/2004 | Michelson |
| 6,752,832 B2 | 6/2004 | Neumann |
| 6,755,841 B2 | 6/2004 | Fraser et al. |
| 6,764,512 B2 | 7/2004 | Keller |
| 6,764,515 B2 | 7/2004 | Ralph et al. |
| 6,767,367 B1 | 7/2004 | Michelson |
| 6,770,074 B2 | 8/2004 | Michelson |
| 6,770,095 B2 | 8/2004 | Grinberg et al. |
| 6,770,096 B2 | 8/2004 | Bolger et al. |
| 6,793,678 B2 | 9/2004 | Hawkins |
| 6,793,679 B2 | 9/2004 | Michelson |

| Patent | Date | Inventor |
|---|---|---|
| 6,800,093 B2 | 10/2004 | Nicholson et al. |
| 6,805,714 B2 | 10/2004 | Sutcliffe |
| 6,808,537 B2 | 10/2004 | Michelson |
| 6,814,737 B2 | 11/2004 | Cauthen |
| 6,824,565 B2 | 11/2004 | Muhanna et al. |
| 6,835,206 B2 | 12/2004 | Jackson |
| 6,849,093 B2 | 2/2005 | Michelson |
| 6,890,355 B2 | 5/2005 | Michelson |
| 6,899,735 B2 | 5/2005 | Coates et al. |
| 6,902,580 B2 | 6/2005 | Fallin et al. |
| 6,916,340 B2 | 7/2005 | Metzger et al. |
| 6,923,811 B1 | 8/2005 | Carl et al. |
| 6,923,830 B2 | 8/2005 | Michelson |
| 6,936,071 B1 * | 8/2005 | Marnay et al. ............ 623/17.15 |
| 6,955,691 B2 | 10/2005 | Chae et al. |
| 6,962,606 B2 | 11/2005 | Michelson |
| 6,964,686 B2 | 11/2005 | Gordon |
| 6,966,929 B2 | 11/2005 | Mitchell |
| 6,972,019 B2 | 12/2005 | Michelson |
| 6,972,035 B2 | 12/2005 | Michelson |
| 6,981,975 B2 | 1/2006 | Michelson |
| 6,984,234 B2 | 1/2006 | Bray |
| 6,984,245 B2 | 1/2006 | McGahan et al. |
| 6,986,789 B2 | 1/2006 | Schultz et al. |
| 6,994,727 B2 | 2/2006 | Khandkar et al. |
| 7,001,385 B2 | 2/2006 | Bonutti |
| 7,001,432 B2 | 2/2006 | Keller et al. |
| 7,008,453 B1 | 3/2006 | Michelson |
| 7,011,684 B2 | 3/2006 | Eckman |
| 7,025,787 B2 | 4/2006 | Bryan et al. |
| 7,033,394 B2 | 4/2006 | Michelson |
| 7,037,340 B2 | 5/2006 | Gau |
| 7,041,135 B2 | 5/2006 | Michelson |
| 7,041,136 B2 | 5/2006 | Goble et al. |
| 7,056,344 B2 | 6/2006 | Huppert et al. |
| 7,060,097 B2 | 6/2006 | Fraser et al. |
| 7,060,099 B2 | 6/2006 | Carli et al. |
| 7,063,701 B2 | 6/2006 | Michelson |
| 7,063,702 B2 | 6/2006 | Michelson |
| 7,066,961 B2 | 6/2006 | Michelson |
| 7,074,237 B2 | 7/2006 | Goble et al. |
| 7,090,698 B2 | 8/2006 | Goble et al. |
| 7,094,239 B1 | 8/2006 | Michelson |
| 7,105,023 B2 | 9/2006 | Eckman |
| 7,105,024 B2 | 9/2006 | Richelsoph |
| 7,112,206 B2 | 9/2006 | Michelson |
| 7,118,579 B2 | 10/2006 | Michelson |
| 7,118,580 B1 | 10/2006 | Beyersdorff et al. |
| 7,118,598 B2 | 10/2006 | Michelson |
| 7,128,760 B2 | 10/2006 | Michelson |
| 7,128,761 B2 | 10/2006 | Kuras et al. |
| 7,153,325 B2 | 12/2006 | Kim et al. |
| 7,163,561 B2 | 1/2007 | Michelson |
| 7,169,153 B2 | 1/2007 | Keller |
| 7,175,662 B2 | 2/2007 | Link et al. |
| 7,179,294 B2 | 2/2007 | Eisermann et al. |
| 7,198,644 B2 | 4/2007 | Schultz et al. |
| 7,204,851 B2 | 4/2007 | Trieu et al. |
| 7,204,852 B2 | 4/2007 | Marnay et al. |
| 7,211,112 B2 | 5/2007 | Baynham et al. |
| 7,217,291 B2 | 5/2007 | Zucherman et al. |
| 7,217,292 B2 | 5/2007 | Ralph et al. |
| 7,217,293 B2 | 5/2007 | Branch, Jr. |
| 7,223,289 B2 | 5/2007 | Trieu et al. |
| 7,232,463 B2 | 6/2007 | Falahee |
| 7,232,464 B2 | 6/2007 | Mathieu et al. |
| 7,291,170 B2 | 11/2007 | Huppert |
| 7,326,248 B2 | 2/2008 | Michelson |
| 7,326,250 B2 | 2/2008 | Beaurain et al. |
| 7,410,501 B2 | 8/2008 | Michelson |
| 7,419,505 B2 | 9/2008 | Fleischmann et al. |
| 7,431,735 B2 | 10/2008 | Liu et al. |
| 7,435,262 B2 | 10/2008 | Michelson |
| 7,442,209 B2 | 10/2008 | Michelson |
| 7,445,635 B2 | 11/2008 | Fallin et al. |
| 7,445,636 B2 | 11/2008 | Michelson |
| 7,455,692 B2 | 11/2008 | Michelson |
| 7,465,317 B2 | 12/2008 | Malberg et al. |
| 7,494,508 B2 | 2/2009 | Zeegers |
| 7,503,933 B2 | 3/2009 | Michelson |
| 7,507,248 B2 | 3/2009 | Beaurain et al. |
| 7,540,882 B2 | 6/2009 | Michelson |
| 7,566,345 B1 | 7/2009 | Fallin et al. |
| 7,588,590 B2 | 9/2009 | Chervitz et al. |
| 7,591,851 B2 | 9/2009 | Winslow et al. |
| 7,594,931 B2 | 9/2009 | Louis et al. |
| 7,594,932 B2 | 9/2009 | Aferzon et al. |
| 7,601,170 B2 | 10/2009 | Winslow et al. |
| 7,608,107 B2 | 10/2009 | Michelson |
| 7,618,453 B2 | 11/2009 | Goble et al. |
| 7,618,455 B2 | 11/2009 | Goble et al. |
| 7,618,456 B2 | 11/2009 | Mathieu et al. |
| 7,621,955 B2 | 11/2009 | Goble et al. |
| 7,621,958 B2 | 11/2009 | Zdeblick et al. |
| 7,632,282 B2 | 12/2009 | Dinville |
| 7,637,951 B2 | 12/2009 | Michelson |
| 7,637,954 B2 | 12/2009 | Michelson |
| 7,641,690 B2 | 1/2010 | Abdou |
| 7,655,027 B2 | 2/2010 | Michelson |
| 7,658,766 B2 | 2/2010 | Melkent et al. |
| 7,682,396 B2 | 3/2010 | Beaurain et al. |
| 7,695,516 B2 | 4/2010 | Zeegers |
| 7,695,517 B2 | 4/2010 | Benzel et al. |
| 7,695,518 B2 | 4/2010 | Gau |
| 7,727,280 B2 | 6/2010 | McLuen |
| 7,749,252 B2 | 7/2010 | Zucherman et al. |
| 7,749,274 B2 | 7/2010 | Razian |
| 7,753,937 B2 | 7/2010 | Chervitz et al. |
| 7,771,473 B2 | 8/2010 | Thramann |
| 7,771,475 B2 | 8/2010 | Michelson |
| 7,776,090 B2 | 8/2010 | Winslow et al. |
| 7,780,670 B2 | 8/2010 | Bonutti |
| 7,789,914 B2 | 9/2010 | Michelson |
| 7,794,502 B2 | 9/2010 | Michelson |
| 7,799,053 B2 | 9/2010 | Haid, Jr. et al. |
| 7,799,057 B2 | 9/2010 | Hudgins et al. |
| 7,799,081 B2 | 9/2010 | McKinley |
| 7,811,326 B2 | 10/2010 | Braddock, Jr. et al. |
| 7,819,903 B2 | 10/2010 | Fraser et al. |
| 7,824,445 B2 | 11/2010 | Biro et al. |
| 7,833,255 B2 | 11/2010 | Chow et al. |
| 7,842,088 B2 | 11/2010 | Rashbaum et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 7,998,211 B2 | 8/2011 | Baccelli et al. |
| 8,002,835 B2 | 8/2011 | Zeegers |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |

| | | |
|---|---|---|
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,114,082 B2 | 2/2012 | Boyajian et al. |
| 2001/0020185 A1 | 9/2001 | Ray |
| 2002/0040243 A1 | 4/2002 | Attali et al. |
| 2002/0087212 A1 | 7/2002 | James et al. |
| 2002/0143343 A1 | 10/2002 | Castro |
| 2002/0161444 A1 | 10/2002 | Choi |
| 2002/0165613 A1 | 11/2002 | Lin et al. |
| 2002/0193880 A1 | 12/2002 | Fraser |
| 2003/0028249 A1 | 2/2003 | Baccelli et al. |
| 2003/0055503 A1 | 3/2003 | O'Neil |
| 2003/0069586 A1 | 4/2003 | Errico et al. |
| 2003/0074075 A1 | 4/2003 | Thomas, Jr. et al. |
| 2003/0093153 A1 | 5/2003 | Banick et al. |
| 2003/0093156 A1 | 5/2003 | Metzger et al. |
| 2003/0109928 A1 | 6/2003 | Pasquet et al. |
| 2003/0135279 A1 | 7/2003 | Michelson |
| 2003/0149438 A1 | 8/2003 | Nichols et al. |
| 2003/0171814 A1 | 9/2003 | Muhanna et al. |
| 2003/0187436 A1 | 10/2003 | Bolger et al. |
| 2003/0187506 A1 | 10/2003 | Ross et al. |
| 2003/0195514 A1 | 10/2003 | Trieu et al. |
| 2003/0220691 A1 | 11/2003 | Songer et al. |
| 2003/0233145 A1 | 12/2003 | Landry et al. |
| 2004/0002758 A1 | 1/2004 | Landry et al. |
| 2004/0002761 A1 | 1/2004 | Rogers et al. |
| 2004/0010312 A1 | 1/2004 | Enayati |
| 2004/0010316 A1 | 1/2004 | William et al. |
| 2004/0024406 A1 | 2/2004 | Ralph et al. |
| 2004/0030387 A1 | 2/2004 | Landry et al. |
| 2004/0034423 A1 | 2/2004 | Lyons et al. |
| 2004/0073309 A1 | 4/2004 | Bianchi et al. |
| 2004/0073311 A1 | 4/2004 | Ferree |
| 2004/0083000 A1 | 4/2004 | Keller et al. |
| 2004/0093082 A1 | 5/2004 | Ferree |
| 2004/0093083 A1 | 5/2004 | Branch et al. |
| 2004/0102846 A1 | 5/2004 | Keller et al. |
| 2004/0111160 A1 | 6/2004 | Evans et al. |
| 2004/0117022 A1 | 6/2004 | Marnay et al. |
| 2004/0133278 A1 | 7/2004 | Marino et al. |
| 2004/0133281 A1 | 7/2004 | Khandkar et al. |
| 2004/0143332 A1 | 7/2004 | Krueger et al. |
| 2004/0148029 A1 | 7/2004 | Bianchi et al. |
| 2004/0153157 A1 | 8/2004 | Keller |
| 2004/0158254 A1 | 8/2004 | Eisermann |
| 2004/0158328 A1 | 8/2004 | Eisermann |
| 2004/0162617 A1 | 8/2004 | Zucherman et al. |
| 2004/0172020 A1 | 9/2004 | Beaurain et al. |
| 2004/0193273 A1 | 9/2004 | Huang |
| 2004/0199254 A1 | 10/2004 | Louis et al. |
| 2004/0210219 A1 | 10/2004 | Bray |
| 2004/0210313 A1 | 10/2004 | Michelson |
| 2004/0220582 A1 | 11/2004 | Keller |
| 2004/0225295 A1 | 11/2004 | Zubok et al. |
| 2004/0225363 A1 | 11/2004 | Richelsoph |
| 2004/0225364 A1 | 11/2004 | Richelsoph |
| 2004/0243238 A1 | 12/2004 | Arnin et al. |
| 2004/0243240 A1 | 12/2004 | Beaurain et al. |
| 2004/0254577 A1 | 12/2004 | Delecrin et al. |
| 2004/0254643 A1 | 12/2004 | Jackson |
| 2005/0010215 A1 | 1/2005 | Delecrin et al. |
| 2005/0015094 A1 | 1/2005 | Keller |
| 2005/0015095 A1 | 1/2005 | Keller |
| 2005/0015149 A1 | 1/2005 | Michelson |
| 2005/0021042 A1 | 1/2005 | Marnay et al. |
| 2005/0027359 A1 | 2/2005 | Mashburn |
| 2005/0027363 A1 | 2/2005 | Gordon |
| 2005/0033305 A1 | 2/2005 | Schultz |
| 2005/0033428 A1 | 2/2005 | Keller |
| 2005/0033435 A1 | 2/2005 | Belliard et al. |
| 2005/0033437 A1 | 2/2005 | Bao et al. |
| 2005/0033438 A1 | 2/2005 | Schultz |
| 2005/0038512 A1 | 2/2005 | Michelson |
| 2005/0043798 A1 | 2/2005 | Eckman |
| 2005/0043800 A1 | 2/2005 | Paul et al. |
| 2005/0043804 A1 | 2/2005 | Gordon et al. |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0065611 A1 | 3/2005 | Huppert et al. |
| 2005/0071009 A1 | 3/2005 | Muhanna et al. |
| 2005/0085911 A1 | 4/2005 | Link |
| 2005/0085917 A1 | 4/2005 | Marnay et al. |
| 2005/0107788 A1 | 5/2005 | Beaurain et al. |
| 2005/0113926 A1 | 5/2005 | Zucherman et al. |
| 2005/0119665 A1 | 6/2005 | Keller |
| 2005/0131542 A1 | 6/2005 | Benzel et al. |
| 2005/0131544 A1 | 6/2005 | Kuras et al. |
| 2005/0143733 A1 | 6/2005 | Petit |
| 2005/0143824 A1 | 6/2005 | Richelsoph et al. |
| 2005/0143825 A1 | 6/2005 | Enayati |
| 2005/0149189 A1 | 7/2005 | Mokhtar et al. |
| 2005/0154462 A1 | 7/2005 | Zucherman et al. |
| 2005/0159818 A1 | 7/2005 | Blain |
| 2005/0165408 A1 | 7/2005 | Puno et al. |
| 2005/0165485 A1 | 7/2005 | Trieu |
| 2005/0171610 A1 | 8/2005 | Humphreys et al. |
| 2005/0192671 A1 | 9/2005 | Bao et al. |
| 2005/0197705 A1 | 9/2005 | Arnin et al. |
| 2005/0197706 A1 | 9/2005 | Hovorka et al. |
| 2005/0216086 A1 | 9/2005 | Marik et al. |
| 2005/0216092 A1 | 9/2005 | Marik et al. |
| 2005/0228500 A1 | 10/2005 | Kim et al. |
| 2005/0234553 A1 | 10/2005 | Gordon |
| 2005/0240273 A1 | 10/2005 | Khandkar et al. |
| 2005/0246024 A1 | 11/2005 | Zeegers |
| 2005/0251260 A1 | 11/2005 | Gerber et al. |
| 2005/0256579 A1 | 11/2005 | Keller et al. |
| 2005/0267581 A1 | 12/2005 | Marnay et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283242 A1 | 12/2005 | Zucherman et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2006/0015183 A1 | 1/2006 | Gilbert et al. |
| 2006/0016768 A1 | 1/2006 | Grichar et al. |
| 2006/0020341 A1 | 1/2006 | Schneid et al. |
| 2006/0030860 A1 | 2/2006 | Peterman |
| 2006/0036261 A1 | 2/2006 | McDonnell |
| 2006/0036325 A1 | 2/2006 | Paul et al. |
| 2006/0036326 A1 | 2/2006 | Baumgartner et al. |
| 2006/0041313 A1 | 2/2006 | Allard et al. |
| 2006/0041314 A1 | 2/2006 | Milliard |
| 2006/0058878 A1 | 3/2006 | Michelson |
| 2006/0069437 A1 | 3/2006 | Weber |
| 2006/0069441 A1 | 3/2006 | Zucherman et al. |
| 2006/0085076 A1 | 4/2006 | Krishna et al. |
| 2006/0085077 A1 | 4/2006 | Cook et al. |
| 2006/0089717 A1 | 4/2006 | Krishna et al. |
| 2006/0095136 A1 | 5/2006 | McLuen |
| 2006/0111783 A1 | 5/2006 | Aflatoon et al. |
| 2006/0116768 A1 | 6/2006 | Krueger et al. |
| 2006/0116769 A1 | 6/2006 | Marnay et al. |
| 2006/0122703 A1 | 6/2006 | Aebi et al. |
| 2006/0129244 A1 | 6/2006 | Ensign |
| 2006/0136063 A1 | 6/2006 | Zeegers |
| 2006/0142863 A1 | 6/2006 | Fraser et al. |
| 2006/0149273 A1 | 7/2006 | Ross et al. |
| 2006/0149371 A1 | 7/2006 | Marik et al. |
| 2006/0149378 A1 | 7/2006 | Chase et al. |
| 2006/0155377 A1 | 7/2006 | Beaurain et al. |
| 2006/0155378 A1 | 7/2006 | Eckman |
| 2006/0173544 A1 | 8/2006 | Gau |
| 2006/0178745 A1 | 8/2006 | Bartish et al. |
| 2006/0178746 A1 | 8/2006 | Bartish, Jr. et al. |
| 2006/0190082 A1 | 8/2006 | Keller et al. |
| 2006/0200241 A1 | 9/2006 | Rothman et al. |

| | | |
|---|---|---|
| 2006/0200242 A1 | 9/2006 | Rothman et al. |
| 2006/0200243 A1 | 9/2006 | Rothman et al. |
| 2006/0206208 A1 | 9/2006 | Michelson |
| 2006/0212123 A1 | 9/2006 | Lechmann et al. |
| 2006/0235520 A1 | 10/2006 | Pannu |
| 2006/0235526 A1 | 10/2006 | Lemaire |
| 2006/0241764 A1 | 10/2006 | Michelson |
| 2006/0253201 A1 | 11/2006 | McLuen |
| 2006/0259143 A1 | 11/2006 | Navarro et al. |
| 2006/0265072 A1 | 11/2006 | Richelsoph |
| 2006/0282074 A1 | 12/2006 | Renaud et al. |
| 2006/0287728 A1 | 12/2006 | Mokhtar et al. |
| 2007/0010886 A1 | 1/2007 | Banick et al. |
| 2007/0010887 A1 | 1/2007 | Williams et al. |
| 2007/0016217 A1 | 1/2007 | Dinville |
| 2007/0016297 A1 | 1/2007 | Johnson |
| 2007/0016299 A1 | 1/2007 | Eckman |
| 2007/0032871 A1 | 2/2007 | Michelson |
| 2007/0055378 A1 | 3/2007 | Ankney et al. |
| 2007/0073403 A1 | 3/2007 | Lombardo et al. |
| 2007/0073404 A1 | 3/2007 | Rashbaum et al. |
| 2007/0088362 A1 | 4/2007 | Bonutti et al. |
| 2007/0100454 A1 | 5/2007 | Burgess et al. |
| 2007/0100455 A1 | 5/2007 | Parsons |
| 2007/0100456 A1 | 5/2007 | Dooris et al. |
| 2007/0118223 A1 | 5/2007 | Allard et al. |
| 2007/0123985 A1 | 5/2007 | Errico et al. |
| 2007/0149974 A1 | 6/2007 | Mangione |
| 2007/0162130 A1 | 7/2007 | Rashbaum et al. |
| 2007/0179623 A1 | 8/2007 | Trieu et al. |
| 2007/0250167 A1 | 10/2007 | Bray et al. |
| 2007/0250168 A1 | 10/2007 | Lechmann et al. |
| 2007/0260249 A1 | 11/2007 | Boyajian et al. |
| 2007/0270951 A1 | 11/2007 | Davis et al. |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2007/0288094 A1 | 12/2007 | Krishna et al. |
| 2007/0299524 A1 | 12/2007 | Rivin |
| 2008/0027547 A1 | 1/2008 | Yu et al. |
| 2008/0027550 A1 | 1/2008 | Link et al. |
| 2008/0033555 A1 | 2/2008 | Link et al. |
| 2008/0033562 A1 | 2/2008 | Krishna et al. |
| 2008/0161930 A1 | 7/2008 | Carls et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0262504 A1 | 10/2008 | Ralph et al. |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0076615 A1 | 3/2009 | Duggal et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2010/0004664 A1 | 1/2010 | Boyajian et al. |
| 2010/0049259 A1 | 2/2010 | Lambrecht et al. |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1 | 9/2011 | Donner et al. |
| 2011/0264227 A1 | 10/2011 | Boyajian et al. |
| 2011/0295371 A1 | 12/2011 | Moskowitz et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0053693 A1 | 3/2012 | Zeegers |

FOREIGN PATENT DOCUMENTS

| | | |
|---|---|---|
| CA | 2533473 | 3/2011 |
| DE | 2263842 A | 7/1974 |
| DE | 2804936 | 8/1979 |
| DE | 3023353 A | 4/1981 |
| DE | 8912648 U | 11/1990 |
| DE | 4328690 | 3/1995 |
| DE | 29911422 | 8/1999 |

| | | |
|---|---|---|
| DE | 20310432 U | 9/2003 |
| DE | 20310433 U | 9/2003 |
| DE | 20320454 | 10/2004 |
| DE | 10323363 | 12/2004 |
| DE | 102004027986 | 7/2005 |
| EP | 42271 | 12/1981 |
| EP | 176728 | 4/1986 |
| EP | 0298235 A | 1/1989 |
| EP | 0317972 A | 5/1989 |
| EP | 0333990 A | 9/1989 |
| EP | 0356112 | 12/1990 |
| EP | 0512529 A | 11/1992 |
| EP | 0560141 A | 9/1993 |
| EP | 0566810 A1 | 10/1993 |
| EP | 0637439 | 2/1995 |
| EP | 0697200 | 2/1996 |
| EP | 0566810 B1 | 5/1996 |
| EP | 0738504 | 10/1996 |
| EP | 0747025 A1 | 12/1996 |
| EP | 0852934 | 7/1998 |
| EP | 0903126 | 3/1999 |
| EP | 0951879 | 10/1999 |
| EP | 0955021 A | 11/1999 |
| EP | 0978258 | 2/2000 |
| EP | 1222903 | 7/2002 |
| EP | 1250898 A1 | 10/2002 |
| EP | 1287795 | 3/2003 |
| EP | 1344506 | 9/2003 |
| EP | 1344508 | 9/2003 |
| EP | 1504733 | 2/2005 |
| EP | 1374808 | 12/2005 |
| FR | 2124815 A | 9/1972 |
| FR | 2372622 | 6/1978 |
| FR | 2632516 A | 2/1989 |
| FR | 2659226 A | 9/1991 |
| FR | 2716619 | 9/1995 |
| FR | 2718635 A1 | 3/1996 |
| FR | 2723841 | 3/1996 |
| FR | 2724108 A | 3/1996 |
| FR | 2730159 A1 | 8/1996 |
| FR | 2737656 A | 2/1997 |
| FR | 2787019 | 12/1998 |
| FR | 2787021 A | 6/2000 |
| FR | 2824261 | 11/2002 |
| FR | 2381796 | 5/2003 |
| FR | 2843293 | 2/2004 |
| FR | 2846550 | 5/2004 |
| FR | 2865629 | 8/2005 |
| FR | 2865630 A1 | 8/2005 |
| FR | 2869528 | 11/2005 |
| FR | 26869528 | 11/2005 |
| FR | 2879436 | 6/2006 |
| FR | 2880795 | 7/2006 |
| FR | 2887762 | 1/2007 |
| FR | 2891135 | 3/2007 |
| FR | 2893838 | 6/2007 |
| FR | 2916956 | 12/2008 |
| GB | 0325421 | 2/1930 |
| JP | 2261446 | 10/1990 |
| WO | WO9011740 | 10/1990 |
| WO | WO9011740 A | 10/1990 |
| WO | WO9107931 | 6/1991 |
| WO | WO9113598 A | 9/1991 |
| WO | WO9301771 A | 2/1993 |
| WO | WO9404100 | 3/1994 |
| WO | WO9515133 | 6/1995 |
| WO | WO9817209 | 4/1998 |
| WO | WO9909914 | 3/1999 |
| WO | WO9953871 | 10/1999 |
| WO | WO9956675 A | 11/1999 |
| WO | WO9956676 | 11/1999 |
| WO | WO9965412 | 12/1999 |
| WO | WO9966864 | 12/1999 |
| WO | WO0053127 A | 9/2000 |
| WO | WO0074606 A | 12/2000 |
| WO | WO0101893 A | 1/2001 |
| WO | WO0119295 A | 3/2001 |
| WO | WO0141680 | 6/2001 |
| WO | WO0143620 | 6/2001 |
| WO | WO0162191 | 8/2001 |
| WO | WO0213732 | 2/2002 |
| WO | WO02058599 | 8/2002 |
| WO | WO02071960 | 9/2002 |
| WO | WO02089701 A2 | 11/2002 |
| WO | WO03005939 | 1/2003 |
| WO | WO03015646 | 2/2003 |
| WO | WO03026522 | 4/2003 |
| WO | WO 03/039400 * | 5/2003 |
| WO | WO03039400 A2 | 5/2003 |
| WO | WO03045262 | 6/2003 |
| WO | WO03059212 A | 7/2003 |
| WO | WO03075803 | 9/2003 |
| WO | WO03075804 A | 9/2003 |
| WO | WO2004034935 | 4/2004 |
| WO | WO2004039291 | 5/2004 |
| WO | WO2004041129 A1 | 5/2004 |
| WO | WO2004041131 | 5/2004 |
| WO | WO2004071360 | 8/2004 |
| WO | WO2004089256 | 10/2004 |
| WO | WO2005007040 | 1/2005 |
| WO | WO2005046534 | 5/2005 |
| WO | WO2005051243 | 6/2005 |
| WO | WO2005074839 | 8/2005 |
| WO | WO2005104996 | 11/2005 |
| WO | WO2005117728 | 12/2005 |
| WO | WO2006016384 | 2/2006 |
| WO | WO2006047587 | 5/2006 |
| WO | WO2006062960 | 6/2006 |
| WO | WO2006120505 | 11/2006 |
| WO | WO2006130460 | 12/2006 |
| WO | WO2006136760 | 12/2006 |
| WO | WO2007000654 | 1/2007 |
| WO | WO2007034310 | 3/2007 |
| WO | WO2007063398 | 6/2007 |
| WO | WO2007078978 | 7/2007 |
| WO | WO2008099277 | 8/2008 |
| WO | WO2008149223 | 12/2008 |
| WO | WO2009033100 | 3/2009 |
| WO | WO2011080535 | 7/2011 |

OTHER PUBLICATIONS

A Multicenter Retrospective Study of the Clinical Results of the Link SB Charite Intervertebral Prosthesis, S.L. Griffith, PhD, A.P. Shelokov, MD, K. Buttner-Janz, MD, Jean-Phillippe LeMaire, MD and W.S. Zeegers, MD, Spine, vol. 19, No. 16, pp. 1842-1849, Mar. 21, 1994.

A New Technique for the Three-Dimensional Study of the Spine in Vitro and In Vivo by Using a Motion-Analysis System, X, Liu, G. Fabry, K. Labey, L. Van Den Berghe, R. Van Audekercke, G. Molenaers, P. Moens, Journal of Spinal Disorders, vol. 10, No. 4, pp. 329-338, Jan. 30, 1997.

Alternatives to Spinal Fusion, J.P. Kostuik, Spinal Fusion, vol. 29, No. 4, Oct. 1998, pp.

Centrode Patterns and Segmental Instability in Degenerative Disc Disease, S.D. Gertzban, MD, FRCSC, J. Seligman, MD, R. Holtby, MD, K.H. Chan, MD, A. Kapasouri, BSc, M. Title, MD, BSc, (MED), FRCSC ©, and B. Cruickshank, MD, FRCPath, Spine, vol. 10, No. 3, pp. 257-261, Jan. 21, 1984.

Clinical Biomechanics of the Spine, A.A. White III, M.M. Panjabi, pp. 128-130, 2nd Edition, J.B. Lippincott Co., 1990.

Computer Analysis of Spinal Segment Motion in Degenerative Disc Disease with and Without Axial Loading, J.V. Seligman, S.D. Gertzbein, M. Tile, A., Kapasouri, Spine, vol. 9., No. 6, pp. 566-573, Dec. 31, 1983.

FR 2 718 635 Preliminary Search Report, National Institute of Industrial Property (France), Jan. 16, 1995.

FR 2 730 159 Preliminary Search Report, National Institute of Industrial Property (France), Sep. 29, 1995.

FR 2 824 261 Preliminary Search Report, National Institute Industrial Property (France), Feb. 25, 2002.

FR 2 831 796 Preliminary Search Report, National Institute of Industrial Property (France), Aug. 2, 2002.

FR 2 846 550 Preliminary Search Report, National Institute of Industrial Property (France), Jul. 10, 2003.

FR 2 865 629 Preliminary Search Report, National Institute of Industrial Property (France), Sep. 14, 2004.
FR 2 865 630 Preliminary Search Report, National Institute of Industrial Property (France), Jan. 12, 2005.
FR 2 869 528 Preliminary Search Report, National Institute of Industrial Property (France), Dec. 13, 2004.
Instantaneous Axis of Rotation as a Function of the Three Columns of the Spine, T.R. Haber, MD, M. O'Brien, MD, W.T. Felmly, MD, D. Welin, MD, G. Perrier, MD, J. Choueka, JD, V. Devlin, MD, A. Vassiliou, ME, and G. Chow, MD, Spine, vol. 17, No. 6, pp. S149-S154, Jan. 9, 1992.
Instantenous Axis of Rotation of the Lumbar Intervertebral Joints, M.J. Pearcy, H. Bogduk, Spine, vol. 13, No. 9, pp. 1033-1041, Nov. 15, 1987.
Mobidisc (website) 1 page, www.Idrmedical.fr/mobidisc.htm, Sep. 19, 2004.
Motion Characteristics of the Normal Lumbar Spine in Young Adults: Instantaneous of Axis of Rotation and Vertebral Center Motion Analysis, t. Yoshioka. H. Tsuji, N. Hirano and S. Sainoh, Journal of Spinal Disorders, vol. 3, No. 2, pp. 103-113, 1990.
PCT/IB02/02998 International Search Report, EPO, Sep. 16, 2003.
PCT/IB02/04642 International Search Report, EPO, Jul. 2, 2003.
PCT/IB05/00280 International Search Report, EPO, Jun. 24, 2005.
PCT/IB05/01151 International Search Report, EPO, Sep. 12, 2005.
PCT/IB03/04872 International Search Report, EPO, Mar. 3, 2004.
PCT/IB02/02998 International Preliminary Examination Report, EPO, Dec. 22, 2003.
PCT/IB02/04642 International Preliminary Examination Report, EPO, Apr. 1, 2004.
PCT/IB03/04872 International Preliminary Examination Report, EPO, Mar. 1, 2005.
Relocation of the Bending Axis During Flexion-Extension of Lumbar intervertebral Discs and its Implications for Prolapse, J.A. Klein and D.W.L. Hukins, Spine, vol. 8, No. 6, pp. 659-664. Nov. 18, 1982.
The Effect of the Three Columns of the Spine on the Instantaneous Axis of Rotation in Flexion and Extension, T. R. Haher, M. Bergman, M. O'Brien, W.T. Felmly, J. Choueka, D. Welin, G. Chow, A. Vassiliou, Spine, vol. 16, No. 8, pp. S312-S318, Apr. 16, 1991.
USPTO OA of Feb. 6, 2007 U.S. Appl. No. 11/109,276.
USPTO OA of Oct. 16, 2007 in U.S. Appl. No. 11/109,276.
USPTO OA of Jul. 24, 2008 in U.S. Appl. No. 11/109,276.
USPTO OA of Feb. 13, 2009 in U.S. Appl. No. 11/109,276.
Applicant's Reply to USPTO OA of Feb. 6, 2007 in U.S. Appl. No. 11/109,276.
Applicant's Reply to USPTO OA of Oct. 16, 2007 in U.S. Appl. No. 11/109,276.
Applicant's Reply to USPTO OA of Jul. 24, 2008 in U.S. Appl. No. 11/109,276.
Applicant's Response to USPTO OA of Feb. 13, 2009 in U.S. Appl. No. 11/109,276.
USPTO OA of Apr. 18, 2007 in U.S. Appl. No. 10/533,846.
Applicant's Response to USPTO OA of Apr. 18, 2007 in U.S. Appl. No. 10/533,846.
USPTO OA of Dec. 26, 2007 in U.S. Appl. No. 10/533,846.
Applicant's Response to USPTO OA of Dec. 26, 2007 in U.S. Appl. No. 10/533,846.
USPTO OA of Oct. 15, 2008 in U.S. Appl. No. 10/533,846.
Applicant's Response to USPTO OA of Oct. 15, 2008 in U.S. Appl. No. 10/533,846.
USPTO OA of Jan. 22, 2008 in U.S. Appl. No. 11/180,868.
Applicant's Response to USPTO OA of Jan. 22, 2008 in U.S. Appl. No. 11/180,868.
USPTO OA of Nov. 5, 2008 in U.S. Appl. No. 11/180,868.
Response to USPTO OA of Nov. 5, 2008 in U.S. Appl. No. 11/180,868.
USPTO OA of Apr. 13, 2009 in U.S. Appl. No. 11/341,007.
USPTO OA of Mar. 20, 2009 in U.S. Appl. No. 11/676,237.
USPTO OA of Feb. 18, 2009 in U.S. Appl. No. 11/632,253.
Applicant's Response to USPTO OA of Feb. 18, 2009 in U.S. Appl. No. 11/632,253.
U.S. Appl. No. 11/378,165, filed Mar. 17, 2006, Transforanimal intersomatic cage for an intervertebral fusion graft and an instrument for implanting the cage.
U.S. Appl. No. 12/279,664, filed Apr. 22, 2009, Transforaminal intersomatic cage for an intervertebral fusion graft and an instrument for implanting the cage.
U.S. Appl. No. 11/767,386, filed Jun. 22, 2007, Intersomatic cage with unified grafts.
U.S. Appl. No. 12/134,884, filed Jun. 6, 2008, Intersomatic cage, intervertebral prosthesis, anchoring device and implantation instruments.
U.S. Appl. No. 12/360,050, filed Jan. 26, 2009, Intervertebral Disc Prosthesis.
U.S. Appl. No. 12/430,768, filed Apr. 27, 2009, Vertebral Cage Device With Modular Fixation.
U.S. Appl. No. 10/492,753, filed Aug. 9, 2004, Progressive approach osteosynthesis device and preassembly method.
U.S. Appl. No. 10/492,827, filed Jul. 15, 2004, Plate for osteosynthesis device and preassembling method.
U.S. Appl. No. 10/498,234, filed Dec. 7, 2004, Implant for Osseous Anchoring with Polyaxial Head.
U.S. Appl. No. 10/570,080, filed Jun. 9, 2006, Osseous anchoring implant with a polyaxial head and method for installing the implant.
U.S. Appl. No. 10/575,065, filed Apr. 7, 2006, Device and method for sectioning a vertebral lamina.
U.S. Appl. No. 11/051,710, filed Feb. 4, 2005, Intervertebral Disc Prosthesis.
U.S. Appl. No. 11/362,253, filed Feb. 24, 2006, Intervertebral Disc Prosthesis and Instrumentation for Insertion of the Prosthesis Between the Vertebrae.
U.S. Appl. No. 11/676,237, filed Feb. 16, 2007, Intervertebral disc prosthesis insertion assemblies.
U.S. Appl. No. 11/874,144, filed Oct. 17, 2007, Modular intervertebral prosthesis.
U.S. Appl. No. 11/958,285, filed Dec. 17, 2007, Vertebral Support Device.
U.S. Appl. No. 12/025,677, filed Feb. 4, 2008, Intervertebral disc prosthesis, surgical methods, and fitting tools.
U.S. Appl. No. 12/172,074, filed Jul. 11, 2008, Transverse spinal linking device and system.
U.S. Appl. No. 12/409,327, filed Mar. 23, 2009, Spinal Osteosynthesis Device and Preparation Method.
U.S. Appl. No. 12/424,364, filed Apr. 15, 2009, Intervertebral Disk Prosthesis.
U.S. Appl. No. 12/435,955, filed May 5, 2009, Instrumentation and Methods for Inserting an Intervertebral Disc Prosthesis.
U.S. Appl. No. 12/527,373, filed Aug. 14, 2009, Intervertebral disc prosthesis insertion assemblies.
U.S. Appl. No. 12/562,704, filed Sep. 18, 2009, Implant for Osseous Anchoring with Polyaxial Head.
U.S. Appl. No. 12/955,898, filed Nov. 29, 2010, Intervertebral Disc Prosthesis.
U.S. Appl. No. 13/158,761, Jun. 13, 2011, Instruments and Methods for Removing Fixation Devices from Intervertebral Implants.
U.S. Appl. No. 13/215,123, filed Aug. 22, 2011, Intervertebral Disc Prosthesis.
U.S. Appl. No. 13/369,560, filed Feb. 9, 2012, Interspinous Implant and Implantation Instrument.
U.S. Appl. No. 13/454,927, filed Apr. 24, 2012, Plate for Osteosynthesis Device and Preassembly Method.
U.S. Appl. No. 13/438,352, filed Apr. 3, 2012, Vertebral Cage Device With Modular Fixation.
World Intellectual Property Organization; International Preliminary Report on Patentability for PCT Pub'n No. WO2005074839; Jan. 16, 2006; WIPO; Geneva, Switzerland; all pages.
World Intellectual Property Organization; Written Opinon of the International Searching Authority for PCT Pub'n No. WO2005074839; Jun. 24, 2005; WIPO; Geneva, Switzerland; all pages.
World Intellectual Property Organization; International Preliminary Report on Patentability for PCT Pub'n No. WO2005104996; Jun. 28, 2006; WIPO; Geneva, Switzerland; all pages.
World Intellectual Property Organization; Written Opinon of the International Searching Authority for PCT Pub'n No. WO2005104996; Sep. 12, 2005; WIPO; Geneva, Switzerland; all pages.

National Institute of Industrial Property (France); Preliminary Search Report in Fench Pub. No. FR2879436; Aug. 11, 2005; National Institute of Industrial Property (France); France; all pages.
World Intellectual Property Organization; International Preliminary Report on Patentability for PCT Pub'n No. WO2006120505; Feb. 22, 2007; WIPO; Geneva, Switzerland; all pages.
World Intellectual Property Organization; International Search Report for PCT Pub'n No. WO2006120505; Aug. 21, 2006; WIPO; Geneva, Switzerland; all pages.
World Intellectual Property Organization; Written Opinon of the International Searching Authority for PCT Pub'n No. WO2006120505; Aug. 21, 2006; WIPO; Geneva, Switzerland; all pages.
National Institute of Industrial Property (France); Preliminary Search Report in Fench Pub. No. FR2887762; Dec. 21, 2005; National Institute of Industrial Property (France); France; all pages.
World Intellectual Property Organization; International Preliminary Report on Patentability for PCT Pub'n No. WO2007000654; Jul. 19, 2007; WIPO; Geneva, Switzerland; all pages.
World Intellectual Property Organization; International Search Report for PCT Pub'n No. WO2007000654; Mar. 14, 2007; WIPO; Geneva, Switzerland; all pages.
World Intellectual Property Organization; Written Opinon of the International Searching Authority for PCT Pub'n No. WO2007000654; Mar. 14, 2007; WIPO; Geneva, Switzerland; all pages.
National Institute of Industrial Property (France); Preliminary Search Report in Fench Pub. No. FR2891135; Jun. 27, 2006; National Institute of Industrial Property (France); France; all pages.
World Intellectual Property Organization; International Preliminary Report on Patentability for PCT Pub'n No. WO2007034310; Aug. 14, 2007; WIPO; Geneva, Switzerland; all pages.
World Intellectual Property Organization; International Search Report for PCT Pub'n No. WO2007034310; Feb. 13, 2007; WIPO; Geneva, Switzerland; all pages.
World Intellectual Property Organization; Written Opinon of the International Searching Authority for PCT Pub'n No. WO2007034310; Feb. 13, 2007; WIPO; Geneva, Switzerland; all pages.
National Institute of Industrial Property (France); Preliminary Search Report in Fench Pub. No. FR2893838; Aug. 4, 2006; National Institute of Industrial Property (France); France; all pages.
World Intellectual Property Organization; International Preliminary Report on Patentability for PCT Pub'n No. WO2007063398; Nov. 12, 2007; WIPO; Geneva, Switzerland; all pages.
World Intellectual Property Organization; International Search Report for PCT Pub'n No. WO2007063398; Jul. 13, 2007; WIPO; Geneva, Switzerland; all pages.
World Intellectual Property Organization; Written Opinon of the International Searching Authority for PCT Pub'n No. WO2007063398; Jul. 13, 2007; WIPO; Geneva, Switzerland; all pages.
National Institute of Industrial Property (France); Preliminary Search Report in Fench Pub. No. FR2916956; Jan. 30, 2008; National Institute of Industrial Property (France); France; all pages.
World Intellectual Property Organization; International Preliminary Report on Patentability for PCT Pub'n No. WO2008149223; Aug. 5, 2009; WIPO; Geneva, Switzerland; all pages.
World Intellectual Property Organization; International Search Report for PCT Pub'n No. WO2008149223; Oct. 31, 2008; WIPO; Geneva, Switzerland; all pages.
World Intellectual Property Organization; Written Opinon of the International Searching Authority for PCT Pub'n No. WO2008149223; Oct. 31, 2008; WIPO; Geneva, Switzerland; all pages.
World Intellectual Property Organization; International Search Report for PCT Pub'n No. WO2011080535; Jan. 24, 2011; WIPO; Geneva, Switzerland; all pages.
World Intellectual Property Organization; International Preliminary Report on Patentability for PCT Pub'n No. WO2008099277; May 29, 2009; WIPO; Geneva, Switzerland; all pages.

World Intellectual Property Organization; International Search Report for PCT Pub'n No. WO2008099277; Nov. 7, 2008; WIPO; Geneva, Switzerland; all pages.
World Intellectual Property Organization; Written Opinon of the International Searching Authority for PCT Pub'n No. WO2008099277; Nov. 7, 2008; WIPO; Geneva, Switzerland; all pages.
LDR Medical, by its attorneys; Amendment after Final in U.S. Appl. No. 10/476,565; Nov. 29, 2007; USPTO; Alexandria, Virgina; All Pages.
U.S. Patent & Trademark Office; Notice of Allowance in U.S. Appl. No. 10/476,565; Nov. 29, 2007; USPTO; Alexandria, Virgina; All Pages.
LDR Medical, by its attorneys; Reply to Office Action in U.S. Appl. No. 10/476,565; Nov. 6, 2007; USPTO; Alexandria, Virgina; All Pages.
U.S. Patent & Trademark Office; Office Action in U.S. Appl. No. 10/476,565; May 7, 2007; USPTO; Alexandria, Virgina; All Pages.
LDR Medical, by its attorneys; Reply to Office Action in U.S. Appl. No. 10/476,565; Jan. 18, 2007; USPTO; Alexandria, Virgina; All Pages.
U.S. Patent & Trademark Office; Office Action in U.S. Appl. No. 10/476,565; Jul. 18, 2006; USPTO; Alexandria, Virgina; All Pages.
LDR Medical, by its attorneys; Reply to Office Action in U.S. Appl. No. 12/025,677; Apr. 9, 2012; USPTO; Alexandria, Virgina; All Pages.
U.S. Patent & Trademark Office; Office Action in U.S. Appl. No. 12/025,677; Oct. 7, 2011; USPTO; Alexandria, Virgina; All Pages.
U.S. Patent & Trademark Office; Notice of Allowance in U.S. Appl. No. 10/494,418; Sep. 20, 2005; USPTO; Alexandria, Virgina; All Pages.
U.S. Patent & Trademark Office; Office Action in U.S. Appl. No. 11/051,710; Dec. 15, 2011; USPTO; Alexandria, Virgina; All Pages.
LDR Medical, by its attorneys; Reply to Office Action in U.S. Appl. No. 11/051,710; Oct. 11, 2011; USPTO; Alexandria, Virgina; All Pages.
U.S. Patent & Trademark Office; Office Action in U.S. Appl. No. 11/051,710; Apr. 11, 2011; USPTO; Alexandria, Virgina; All Pages.
LDR Medical, by its attorneys; Reply to Office Action in U.S. Appl. No. 11/051,710; Jan. 20, 2011; USPTO; Alexandria, Virgina; All Pages.
U.S. Patent & Trademark Office; Office Action in U.S. Appl. No. 11/051,710; Jul. 20, 2010; USPTO; Alexandria, Virgina; All Pages.
LDR Medical, by its attorneys; Reply to Office Action in U.S. Appl. No. 11/051,710; Apr. 26, 2010; USPTO; Alexandria, Virgina; All Pages.
U.S. Patent & Trademark Office; Office Action in U.S. Appl. No. 11/051,710; Oct. 26, 2009; USPTO; Alexandria, Virgina; All Pages.
U.S. Patent & Trademark Office; Notice of Allowance in U.S. Appl. No. 11/098,266; Apr. 21, 2008; USPTO; Alexandria, Virgina; All Pages.
LDR Medical, by its attorneys; Reply to Office Action in U.S. Appl. No. 11/098,266; Feb. 26, 2008; USPTO; Alexandria, Virgina; All Pages.
U.S. Patent & Trademark Office; Office Action in U.S. Appl. No. 11/098,266; Aug. 6, 2007; USPTO; Alexandria, Virgina; All Pages.
LDR Medical, by its attorneys; Reply to Office Action in U.S. Appl. No. 11/098,266; May 23, 2007; USPTO; Alexandria, Virgina; All Pages.
U.S. Patent & Trademark Office; Office Action in U.S. Appl. No. 11/098,266; Nov. 29, 2006; USPTO; Alexandria, Virgina; All Pages.
LDR Medical, by its attorneys; Reply to Office Action in U.S. Appl. No. 11/098,266; Aug. 22, 2006; USPTO; Alexandria, Virgina; All Pages.
U.S. Patent & Trademark Office; Office Action in U.S. Appl. No. 11/098,266; Mar. 22, 2006; USPTO; Alexandria, Virgina; All Pages.
U.S. Patent & Trademark Office; Notice of Allowance in U.S. Appl. No. 12/391,086; Apr. 15, 2011; USPTO; Alexandria, Virgina; All Pages.
LSR Medical, by its attorneys; Reply to Office Action in U.S. Appl. No. 12/391,086; Jan. 31, 2011; USPTO; Alexandria, Virgina; All Pages.

U.S. Patent & Trademark Office; Office Action in U.S. Appl. No. 12/391,086; Jul. 29, 2010; USPTO; Alexandria, Virgina; All Pages.

U.S. Patent & Trademark Office; Notice of Allowance in U.S. Appl. No. 12/360,050; Mar. 26, 2012; USPTO; Alexandria, Virgina; All Pages.

LDR Medical, by its attorneys; Reply to Office Action in U.S. Appl. No. 12/360,050; Mar. 6, 2012; USPTO; Alexandria, Virgina; All Pages.

U.S. Patent & Trademark Office; Office Action in U.S. Appl. No. 12/360,050; Sep. 6, 2011; USPTO; Alexandria, Virgina; All Pages.

LDR Medical, by its attorneys; Reply to Office Action in U.S. Appl. No. 12/360,050; Jun. 16, 2011; USPTO; Alexandria, Virgina; All Pages.

U.S. Patent & Trademark Office; Office Action in U.S. Appl. No. 12/360,050; Dec. 17, 2010; USPTO; Alexandria, Virgina; All Pages.

LDR Medical, by its attorneys; Reply to Office Action in U.S. Appl. No. 12/435,955; Apr. 11, 2012; USPTO; Alexandria, Virgina; All Pages.

U.S. Patent & Trademark Office; Office Action in U.S. Appl. No. 12/435,955; Oct. 11, 2011; USPTO; Alexandria, Virgina; All Pages.

U.S. Patent & Trademark Office; Notice of Allowance in U.S. Appl. No. 11/341,007; Jun. 26, 2010; USPTO; Alexandria, Virgina; All Pages.

LDR Medical, by its attorneys; Reply to Office Action in U.S. Appl. No. 11/341,007; Jun. 17, 2010; USPTO; Alexandria, Virgina; All Pages.

U.S. Patent & Trademark Office; Office Action in U.S. Appl. No. 11/341,007; Dec. 17, 2009; USPTO; Alexandria, Virgina; All Pages.

LDR Medical, by its attorneys; Reply to Office Action in U.S. Appl. No. 11/341,007; Oct. 13, 2009; USPTO; Alexandria, Virgina; All Pages.

U.S. Patent & Trademark Office; Office Action in U.S. Appl. No. 11/341,007; Apr. 13, 2009; USPTO; Alexandria, Virgina; All Pages.

LDR Medical, by its attorneys; Reply to Office Action in U.S. Appl. No. 12/955,898; Apr. 19, 2012; USPTO; Alexandria, Virgina; All Pages.

U.S. Patent & Trademark Office; Office Action in U.S. Appl. No. 12/955,898; Mar. 19, 2012; USPTO; Alexandria, Virgina; All Pages.

LDR Medical, by its attorneys; Appeal Brief in U.S. Appl. No. 11/362,253; Apr. 9, 2012; USPTO; Alexandria, Virgina; All Pages.

U.S. Patent & Trademark Office; Office Action in U.S. Appl. No. 11/362,253; Mar. 8, 2011; USPTO; Alexandria, Virgina; All Pages.

LDR Medical, by its attorneys; Reply to Office Action in U.S. Appl. No. 11/362,253; Dec. 20, 2010; USPTO; Alexandria, Virgina; All Pages.

U.S. Patent & Trademark Office; Office Action in U.S. Appl. No. 11/362,253; Jun. 18, 2010; USPTO; Alexandria, Virgina; All Pages.

LDR Medical, by its attorneys; Reply to Office Action in U.S. Appl. No. 11/362,253; Apr. 15, 2010; USPTO; Alexandria, Virgina; All Pages.

U.S. Patent & Trademark Office; Office Action in U.S. Appl. No. 11/362,253; Oct. 15, 2009; USPTO; Alexandria, Virgina; All Pages.

LDR Medical, by its attorneys; Reply to Office Action in U.S. Appl. No. 11/362,253; Aug. 18, 2009; USPTO; Alexandria, Virgina; All Pages.

U.S. Patent & Trademark Office; Office Action in U.S. Appl. No. 11/362,253; Feb. 18, 2009; USPTO; Alexandria, Virgina; All Pages.

U.S. Patent & Trademark Office; Office Action in U.S. Appl. No. 12/134,884; Jan. 31, 2012; USPTO; Alexandria, Virgina; All Pages.

U.S. Patent & Trademark Office; Office Action in U.S. Appl. No. 11/676,237; Feb. 16, 2012; USPTO; Alexandria, Virgina; All Pages.

LDR Medical, by its attorneys; Appeal Brief in U.S. Appl. No. 11/676,237; Oct. 17, 2011; USPTO; Alexandria, Virgina; All Pages.

U.S. Patent & Trademark Office; Office Action in U.S. Appl. No. 11/676,237; Sep. 15, 2010; USPTO; Alexandria, Virgina; All Pages.

LDR Medical, by its attorneys; Reply to Office Action in U.S. Appl. No. 11/676,237; Jun. 18, 2010; USPTO; Alexandria, Virgina; All Pages.

U.S. Patent & Trademark Office; Office Action in U.S. Appl. No. 11/676,237; Dec. 18, 2009; USPTO; Alexandria, Virgina; All Pages.

LDR Medical, by its attorneys; Reply to Office Action in U.S. Appl. No. 11/676,237; Sep. 21, 2009; USPTO; Alexandria, Virgina; All Pages.

U.S. Patent & Trademark Office; Office Action in U.S. Appl. No. 11/676,237; Mar. 20, 2009; USPTO; Alexandria, Virgina; All Pages.

U.S. Patent & Trademark Office; Office Action in U.S. Appl. No. 12/527,373; Dec. 12, 2011; USPTO; Alexandria, Virgina; All Pages.

U.S. Patent & Trademark Office; Office Action in U.S. Appl. No. 12/955,898; Jun. 1, 2012; USPTO; Alexandria, Virgina; All Pages.

U.S. Patent & Trademark Office; Examiner's Answer to Appeal Brief in U.S. Appl. No. 11/362,253; Jun. 20, 2012; USPTO; Alexandria, Virgina; All Pages.

U.S. Patent & Trademark Office; Office Action in U.S. Appl. No. 12/025,677; Jun. 29, 2012; USPTO; Alexandria, Virgina; All Pages.

U.S. Patent & Trademark Office; Notice of Allowance in U.S. Appl. No. 12/360,050; Jul. 6, 2012; USPTO; Alexandria, Virginia; All Pages.

LDR Medical, by its attorneys; Reply to Office Action in U.S. Appl. No. 12/527,373; Jun. 21, 2012; USPTO; Alexandria, Virginia; All Pages.

* cited by examiner

INTERVERTEBRAL DISC PROSTHESIS

CROSS-REFERENCE TO RELATED APPLICATIONS

This application is a continuation of U.S. patent application Ser. No. 10/533,846, filed Nov. 11, 2005 now U.S. Pat. No. 7,682,396, which claims priority to International Application PCT/IB03/004872, filed Oct. 31, 2003, which claims priority to French Patent Application No. 0213833, filed Nov. 5, 2002.

BACKGROUND

The present invention relates to an intervertebral disk prosthesis, intended to substitute the fibrocartilaginous disks joining the vertebrae in the spinal column, particularly on the cervical spine.

Various types of prosthesis are known in the prior art. Some of these prostheses, either because they are made of compressible material or because they allow excessive movement of the different constituent parts of the prosthesis with respect to each other, may induce relatively easily the ejection of at least one part of the prosthesis outside the vertebrae, which is not desirable for the patient.

SUMMARY

The purpose of the present invention is to remedy some drawbacks of the prior art by proposing a simple intervertebral disk prosthesis which makes it possible to limit the movements of the different constituent parts of the prosthesis with respect to each other.

This purpose is achieved by an intervertebral disk prosthesis comprising at least three parts including a first plate, referred to as the upper plate, a second plate, referred to as the lower plate, and a core, the upper surface of the core being in contact with at least part of the lower surface of the upper plate and the lower surface of the core being in contact with at least part of the upper surface of the lower plate, and the lower plate being movable at least with respect to the core, characterised in that there are cooperation means between the lower plate and the core, so as to limit or eliminate translation movements of the core with respect to the lower plate, along an axis substantially parallel to the lower plate, and to limit or eliminate rotation movements of the core with respect to the lower plate, around an axis substantially perpendicular to the lower plate, the planes passing through the upper and lower plates forming a substantially constant angle.

According to another feature, the lower plate-comprises male means cooperating with female means of the core.

According to another feature, the lower plate comprises female means cooperating with male means of the core.

According to another feature, the angle is obtained in that the core forms an acute angle in the front-rear direction.

According to another feature, the same plates can be assembled with cores of different thicknesses.

According to another feature, the angle between the upper and lower plates is between 0.degree. and 15.degree.

According to another feature the core is movable with respect to the upper and/or lower plates, which makes it possible to compensate for positioning defects of the three parts of the prosthesis with respect to each other.

According to another feature, at least part of the lower surface of the upper plate is concave and complementary to the upper surface of the core.

According to another feature, the dimensions of each male means are slightly less than those of each female means so as to enable a slight clearance between the core and the lower plate.

According to another feature, the dimensions of each male means are substantially the same as those of each female means so as to prevent any clearance between the core and the lower plate.

According to another feature, the male means of the lower plate are two pins curved towards the inside of the prosthesis and located opposite each other on two edges of the prosthesis, and in that the female means of the core are two recesses.

According to another feature, at least one of the pins is replaced by a lug equipped with a drilling whereon a tag is fixed using a dowel entering the drilling.

According to another feature, the male means of the lower plate are two dowel pins located in the vicinity of the centre of the lower plate, and in that the female means of the core are two wells.

According to another feature, the male means of the lower plate are two walls located opposite each other in the vicinity of two edges of the prosthesis, and in that the female means of the core are recesses.

According to another feature, the male means of the lower plate are a rib located at the centre of the prosthesis, and in that the female means of the core are a groove.

According to another feature, the core is made of polyethylene.

According to another feature, the lower plate comprises one or more openings in the vicinity of its front side, provided to receive prosthesis anchoring means in a vertebra.

According to another feature, the opening of the lower plate is rectangular, and in that the anchoring means consist of a body, forming an acute angle with the lower plate, and a head.

According to another feature, the openings of the lower plate are circular, and in that the anchoring means are nail-shaped.

According to another feature, the upper plate is convex on at least part of its upper surface to fit into the shape of the vertebrae.

Other features and advantages of the present invention will be seen more clearly upon reading the description below, with reference to the appended figures, wherein:

The details of one or more embodiments of the invention are set forth in the accompanying drawings and the description below. Other features, objects, and advantages of the invention will be apparent from the description and drawings, and from the claims.

DETAILED DESCRIPTION

The intervertebral disk prosthesis according to the invention is constituted of an upper plate 1 which is articulated with respect to a lower plate 2 by means of a core 3, as can particularly be seen in FIGS. 4a, 4b, 5a and 6a. One advantage of the prosthesis according to the invention is that it comprises simple parts which can be designed so that the prosthesis is fitted on the cervical spine.

Figure 1A:
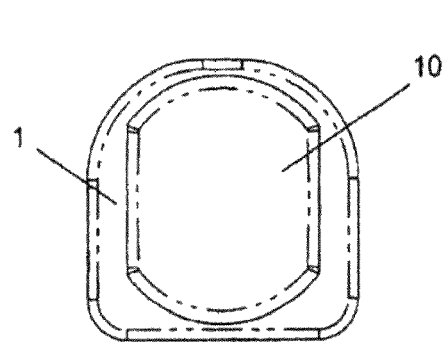
FIGS. 1a and 1b respectively represent a bottom view and a perspective bottom view of the upper plate according to one embodiment, FIGS. 2a and 2b respectively represent a top view and a perspective top view of the lower plate according to one embodiment, FIGS. 3a and 3b respectively represent a top view and a perspective top view of the core according to one embodiment, FIGS. 4a and 4b respectively represent a perspective top view and a side view of the intervertebral disk prosthesis according to the embodiment of FIGS. 1a, 1b, 2a, 2b, 3a and 3b, FIGS. 5a and 5b respectively represent a side view and a sectional view along the plane D-D of FIG. 5a of the intervertebral disk prosthesis according to a second embodiment.
Figure 1B:
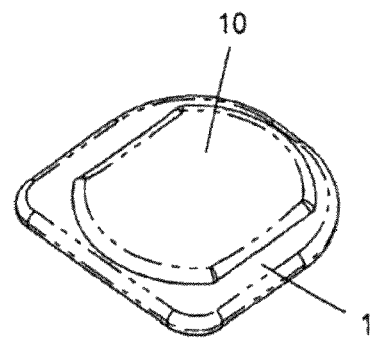
Figure 2A:
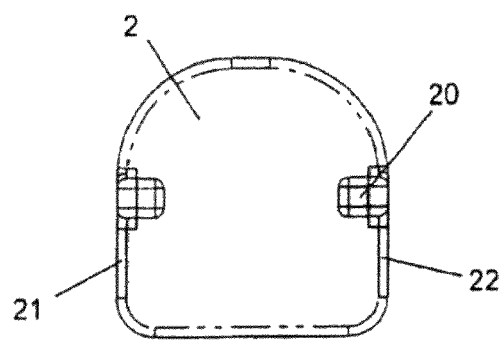
Figure 2B:
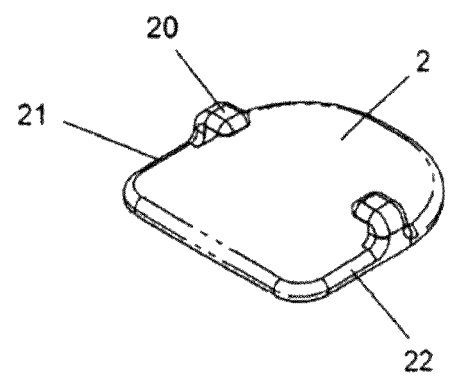

The upper plate 1, particularly visible in FIGS. 1a and 1b, is slightly concave on at least part 10 of its lower surface, so as to fit with the slightly convex upper surface of the core 3. The upper surface of the core 3 is complementary to the concave part 10 of the upper plate 1, enabling movement between the upper plate 1 and the core 3.

Figure 10A:
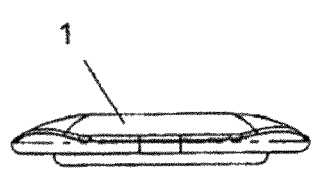
Figure 10B:

In an alternative embodiment, part of the upper surface of the upper plate 1 is convex, as shown in FIGS. 10a and 10b, in order to fit better onto the vertebra whereon the prosthesis is to be fitted, the bottom of the vertebrae being concave. In this case, the convex part of the upper plate 1 is located in the front part of the upper plate, as can particularly be seen in FIG. 10b.

Figure 3A:
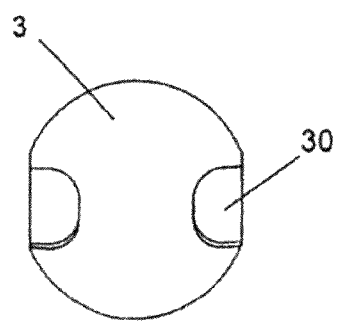
Figure 3B:
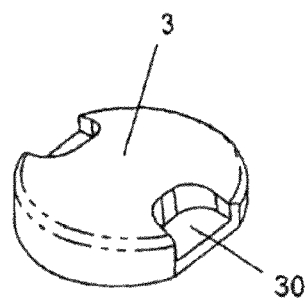

The lower plate 2 is substantially plane. In effect, its lower surface does not need to be convex or concave since the top of the vertebrae is substantially flat. In the embodiment of FIGS. 2a, 2b, 7a and 8a, the lower plate 2 comprises two pins 20 located opposite, each other on two substantially parallel edges 21, 22 of the lower plate 2. Each pin 20 is curved towards the inside of the prosthesis and can thus enter recesses 30 located on the core 3. The core 3, particularly visible in FIGS. 3a and 3b, comprises a substantially plane lower surface, provided to fit onto the lower plate 2. The core 3 is thin (for example 3 mm thick) for a cervical prosthesis or thicker (for example 15 mm) for a lumbar prosthesis.

In the embodiment of FIGS. 3a, 3b, 4a and 4b, the dimensions of each recess 30 of the core 3 are slightly greater than those of each pin 20 of the lower plate 2 so as to limit the clearance of the core 3 with respect to the lower plate 2, both in translation along an axis substantially parallel with the lower plate 2, and in rotation around an axis substantially perpendicular to the lower plate 2. The movement between the upper plate 1 and the core 3, as well as the clearance of the core 3 with respect to the lower plate 2, thus enable the patient to move and, if required, compensate for prosthesis positioning defects. This clearance also offers the advantage of preventing premature wear due to the stress applied to the prosthesis.

Figure 5A:
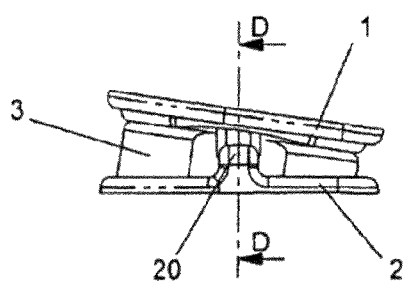
Figure 5B:
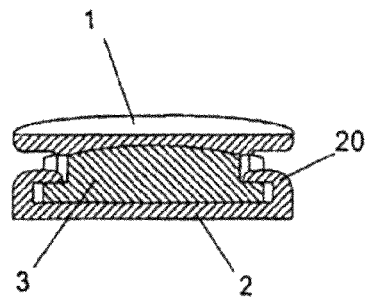
Figure 6A:
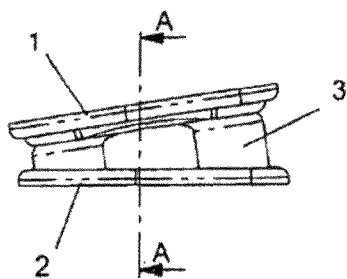
FIG. 6a represents a side view of the intervertebral disk prosthesis according to a third embodiment.
Figure 6B:
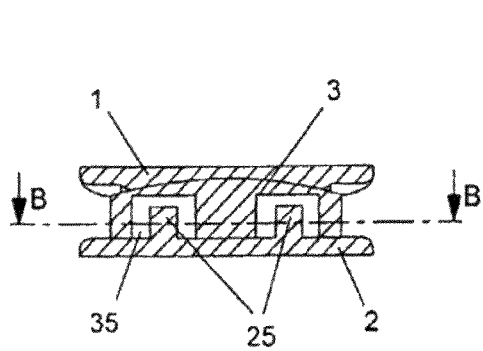
FIGS. 6b and 6d represent a sectional view along the plane A-A of FIG. 6a, the core having, respectively, a slight clearance and no clearance with respect to the lower plate.
Figure 6C:
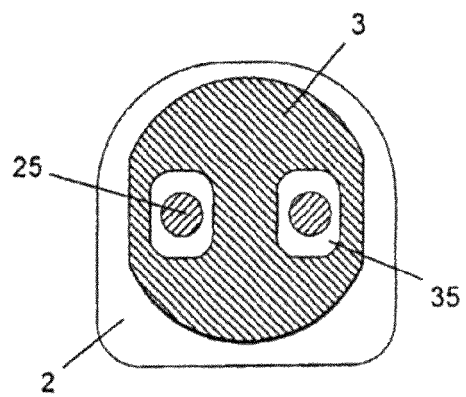
FIGS. 6c and 6e represent a sectional view along the plane B-B of FIGS. 6b and 6d, respectively, of the intervertebral disk prosthesis, FIGS. 7a and 8a respectively represent a top view and perspective bottom view of the lower plate according to two other embodiments, FIGS. 7b and 8b respectively represent a perspective side view and a perspective top view of the lower plate of FIGS. 7a and 8a, respectively, wherein prosthesis anchoring means are inserted according to two different embodiments.
Figure 6D:
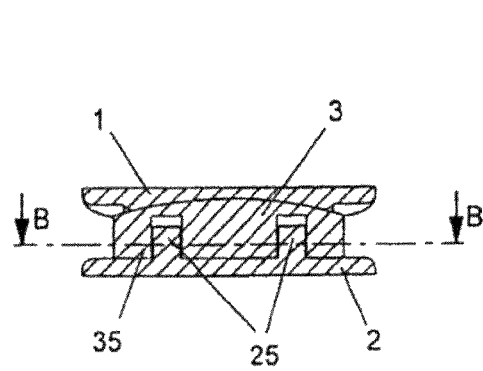
Figure 6E:
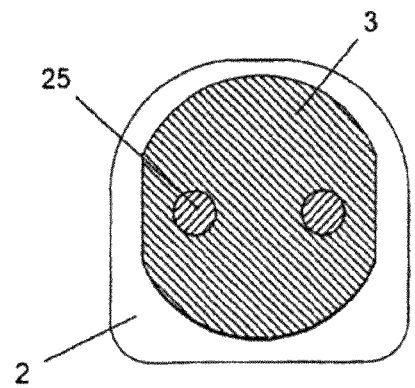

In the embodiment of FIGS. 5a and 5b, the dimensions of each recess 30 of the core 3 are substantially the same as those of each pin 20 of the lower plate 2, so as to prevent any clearance of the core 3 with respect to the lower plate 2, both in translation and rotation. In the latter case, the only movement of the prosthesis authorised is that of the upper plate 1 with respect to the core 3.

Figure 9A:
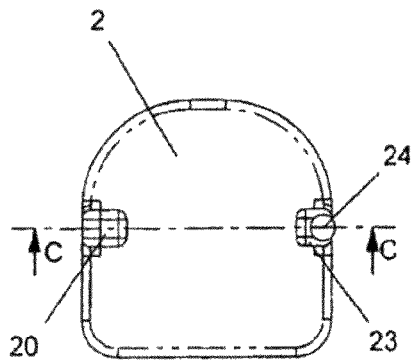
FIG. 9a represents a top view of the lower plate according to a fourth embodiment.
Figure 9B:
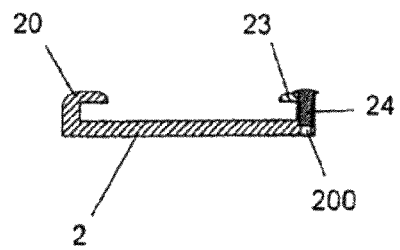
FIG. 9b represents a sectional view of the lower plate along the plane plan C-C of FIG. 9a, FIGS. 10a and 10b respectively represent a rear and side view of the upper plate according to another embodiment.

In the embodiment in FIGS. 9a and 9b, one of the pins 20 is replaced by a lug equipped with a drilling 200. A tag 23 fixes on the lug by means of a dowel 24 entering the drilling 200. In an alternative embodiment, both pins are replaced by a lug whereon a tag 23 is fixed.

In the embodiment of FIGS. 6a, 6b, 6c, 6d and 6e, the lower plate 2 does not comprise any pins 20 but two dowel pins 25 located in the vicinity of the centre of the lower plate 2. In this case, the core 3, by complementarity, does not comprise any recesses 30, but two wells 35 under its lower surface. The dimensions of the dowel pins 25 of the lower plate 2 and of the wells 35 of the core 3 are such that, in the alternative embodiment represented in FIGS. 6b and 6c, a slight clearance in translation and rotation is permitted, and in the alternative embodiment represented in FIGS. 6d and 6e, no clearance is permitted.

In another embodiment, not shown, the lower plate 2 comprises a rib on its upper surface and no pins 20 or dowel pins 25. The core 3, by complementarity, comprises a groove under its lower surface. The dimensions of the rib of the lower plate and the groove of the core are such that, in one alternative embodiment, a slight clearance in translation and rotation is permitted, and in another alternative embodiment, no clearance is permitted.

In another embodiment not shown, the lower plate 2 comprises, instead of the pins 20, two walls, arranged opposite each other, in the vicinity of two substantially parallel edges 21, 22 of the lower plate, but further in the prosthesis than the pins 20. The core 3 comprises complementary recesses with respect to the walls. The dimensions of each recess of the core in this embodiment are, either slightly greater, or substantially the same as those of each wall of the lower plate, so as to enable a slight clearance in translation and rotation or not.

In a further embodiment not shown, the female components are located on the lower plate and the male components on the core.

Figure 4A:
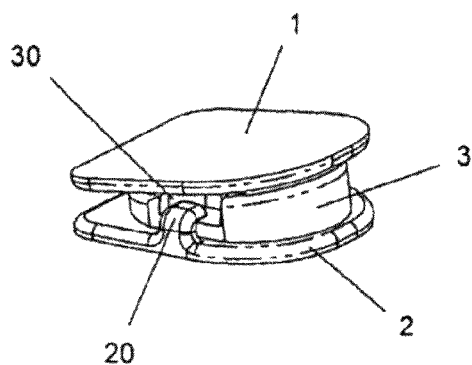
Figure 4B:
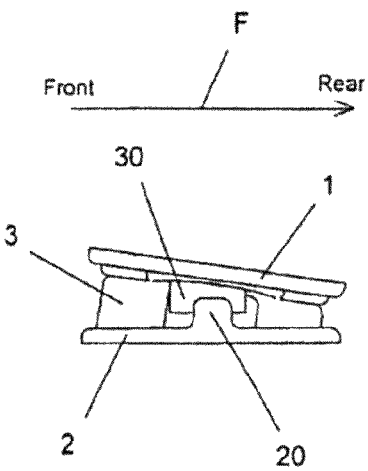

The intervertebral disk prosthesis according to the invention particularly makes it possible to correct lordosis defects and to add lordosis to the spine, for example the cervical spine. Therefore, the presence of an acute angle in the front-rear direction F. FIG. 4b, between the upper plate 1 and the lower plate 2 of the prosthesis is necessary. For example, this angle is between 0.degree. and 15.degree. To adjust the angle required according to the patient, it is simply necessary to select a core 3 with a suitable angle between the mean plane representing its upper surface and the plane passing through its lower surface.

When the female components are located on the lower plates and the male components on the core, the lordotic core, in that it forms an acute angle in the front-rear direction, may then be integral with the plate by a projection entering a cavity or opening of the lower plate.

The inclination of the prostheses known in the prior art is obtained, either by the shape of the upper plate, when the core is flat, or by the position of the upper plate with respect to the core, when said core is convex. With respect to the first case of the prior art mentioned here, the machining of the prosthesis according to the present invention is more economical since the core is composed of a less expensive material (for example, polyethylene) than that composing the plates. With respect to the second case of the prior art mentioned here, the core of the present invention is not liable to be ejected outside the prosthesis since the angle between the plates is substantially constant when the prosthesis is in place.

If surgeons require a determined lordosis for one patient, they will select a core 3 allowing no clearance with respect to the lower plate 2. On the other hand, if they simply require the lordosis to remain within a range of values, they will select a core allowing a slight clearance in translation and rotation with respect to the lower plate 2.

The intervertebral disk prosthesis according to the invention may, in one alternative embodiment, represented in FIGS. 7a, 7b, 8a and 8b, be anchored in the spinal column to prevent the prosthesis from migrating under the effect of the transversal resultant of the force exerted by the spinal column on the prosthesis in place, which increases with the lordosis. In this case, the lower plate 2 comprises one or more openings 28, 29 located in the vicinity of the rear side of the prosthesis, making it possible to receive anchoring means 4, 5.

Figure 7A:
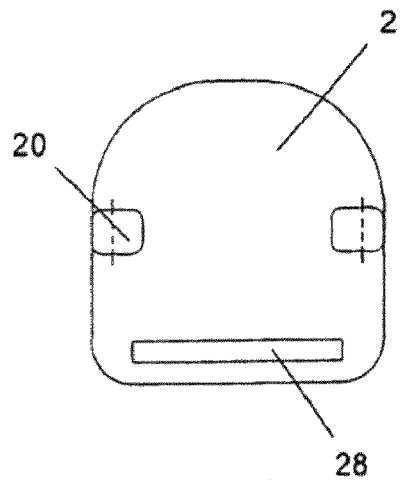
Figure 7B:
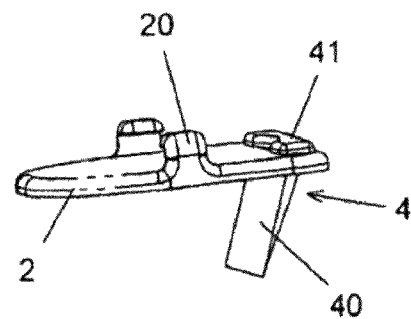

In this way, in the case of FIGS. 7a and 7b, the opening 28 of the lower plate 2 is rectangular and the anchoring means 4 is constituted of a body 40 and a head 41. The dimensions of the head 41 are slightly greater than those of the opening 28 of the lower plate 2, such that, once the anchoring means 4 are in place in a vertebra, the lower plate 2 is sandwiched between the head 41 of the anchoring means 4 and said vertebra. An angle, less than or equal to 90.degree., is comprised between the body 40 of the anchoring means 4 and the lower plate 2.

Figure 8A:
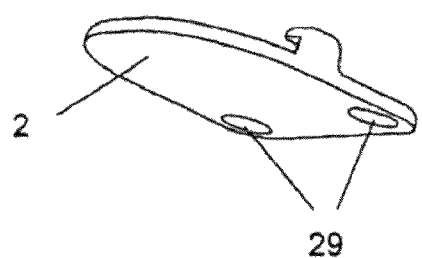
Figure 8B:
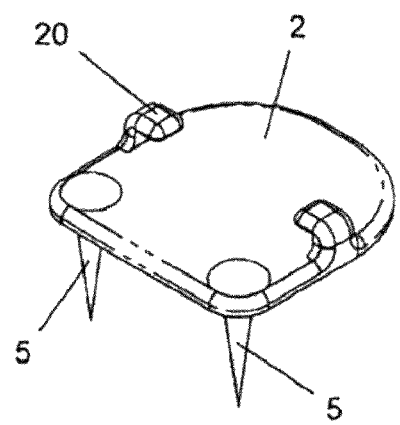

In the case of FIGS. 8a and 8b, two circular openings 29 are comprised in the lower plate 2 and the anchoring means 5 are nail-shaped, with a head of greater dimensions than those of the openings 29 to make it possible to sandwich the lower plate 2 between the head of the anchoring means 5 and the vertebra whereon the prosthesis is anchored.

It should be clear to those skilled in art that the present invention enables embodiments in numerous other specific forms without deviating from the scope of the invention as claimed. Consequently, the present embodiments must be considered as illustrations, but may be modified in the field defined by the scope of the attached claims, and the invention must not be limited to the details given above.

The invention claimed is:

1. An intervertebral disc prosthesis for substitution of a fibrocartilaginous disc between adjacent vertebra in a spinal column comprising:
   an upper plate having a curved lower surface;
   a lower plate having an upper surface;
   a core having an upper surface and a lower surface,
      the upper surface of the core being curved and configured for contact with at least part of the curved lower surface of the upper plate and
      the lower surface of the core being configured for contact with at least part of the upper surface of the lower plate, said contact of the lower surface of the core with at least part of the upper surface of the lower plate being configured for translation movements of the core with respect to the lower plate along an axis substantially parallel to the upper surface of the lower plate and for rotation movements of the core with respect to the lower plate around an axis substantially perpendicular to the upper surface of the lower plate when the intervertebral disc prosthesis is assembled; and
   a stop comprising a male portion and a female portion each located along an edge of the prosthesis, the male portion and the female portion each configured to limit translation movements of the core with respect to lower plate and rotation movements of the core with respect to the lower plate.

2. An intervertebral disc prosthesis according to claim 1 in which the upper surface of the core is convex and the lower surface of the upper plate is concave, and the lower surface of the core and the upper surface of the lower plate are each substantially planar.

3. An intervertebral disc prosthesis according to claim 2 in which the upper plate has an upper surface that is convex and the lower plate has a lower surface that is substantially planar.

4. An intervertebral disc prosthesis according to claim 3 further comprising anchors configured to engage an adjacent vertebra.

5. An intervertebral disc prosthesis according to claim 4 in which the anchors are disposed on opposite sides of the prosthesis.

6. An intervertebral disc prosthesis according to claim 1 in which the female portion is disposed on the lower plate and the male portion is disposed on the core.

7. An intervertebral disc prosthesis according to claim 1 in which the male portion is disposed on the lower plate and the female portion is disposed on the core.

8. An intervertebral disc prosthesis according to claim 7 in which the female portion is a recess.

9. An intervertebral disc prosthesis according to claim 8 in which the recess is a groove.

10. An intervertebral disc prosthesis according to claim 7 in which the male portion is a pin.

11. An intervertebral disc prosthesis according to claim 7 in which the male portion is a wall.

12. An intervertebral disc prosthesis according to claim 1 in which the core forms an acute angle in a front-rear direction.

13. An intervertebral disc prosthesis according to claim 1 in which the core is selected from an assortment of cores having different thicknesses.

14. An intervertebral disc prosthesis for substitution of a fibrocartilaginous disc between adjacent vertebra in a spinal column comprising:
   an upper plate having a curved lower surface;
   a lower plate having an upper surface;
   a core having an upper surface and a lower surface,
   the upper surface of the core being curved and configured for contact with at least part of the curved lower surface of the upper plate and
   the lower surface of the core being configured for contact with at least part of the upper surface of the lower plate, said contact of the lower surface of the core with at least part of the upper surface of the lower plate being configured for translation movements of the core with respect to the lower plate along an axis substantially parallel to the lower plate and for rotation movements of the core with respect to the upper surface of the lower plate around an axis substantially perpendicular to the upper surface of the lower plate when the intervertebral disc prosthesis is assembled; and
   a restraint comprising a stop and a recess each located in the vicinity of an edge of the prosthesis, the stop and the recess each configured to limit translation movements of the core with respect to lower plate and rotation movements of the core with respect to the lower plate.

15. An intervertebral disc prosthesis according to claim 14 in which the upper surface of the core is convex and the lower surface of the upper plate is concave, and the lower surface of the core and the upper surface of the lower plate are each substantially planar.

16. An intervertebral disc prosthesis according to claim 15 in which the upper plate has an upper surface that is convex and the lower plate has a lower surface that is substantially planar.

17. An intervertebral disc prosthesis according to claim 16 further comprising anchors configured to engage an adjacent vertebra.

18. An intervertebral disc prosthesis according to claim 17 in which the anchors are disposed on opposite sides of the prosthesis.

19. An intervertebral disc prosthesis according to claim 14 in which the stop is a wall.

20. An intervertebral disc prosthesis according to claim 14 in which the stop is a pin.

21. An intervertebral disc prosthesis according to claim 14 in which the stop is a lug.

22. An intervertebral disc prosthesis according to claim 14 in which the recess is a groove.

* * * * *